United States Patent
Abe et al.

(10) Patent No.: US 8,474,302 B2
(45) Date of Patent: Jul. 2, 2013

(54) SENSOR CONTROL UNIT AND GAS DETECTION APPARATUS

(75) Inventors: Satoru Abe, Aichi (JP); Yasuhiro Ishiguro, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 806 days.

(21) Appl. No.: 12/639,745

(22) Filed: Dec. 16, 2009

(65) Prior Publication Data

US 2010/0180665 A1 Jul. 22, 2010

(30) Foreign Application Priority Data

Dec. 18, 2008 (JP) ................................. 2008-321839

(51) Int. Cl.
*G01M 15/10* (2006.01)
(52) U.S. Cl.
USPC .......... 73/23.31; 73/31.05; 204/424; 204/426
(58) Field of Classification Search
USPC ...................... 73/23.2, 23.31, 31.05; 204/406, 204/424
See application file for complete search history.

(56) References Cited

U.S. PATENT DOCUMENTS

| | | | |
|---|---|---|---|
| 5,942,190 A | 8/1999 | Kato et al. | |
| 7,288,175 B2* | 10/2007 | Hada et al. | 204/424 |
| 7,309,669 B2* | 12/2007 | Sumi et al. | 501/32 |
| 2009/0114536 A1* | 5/2009 | Ishiguro et al. | 204/406 |
| 2009/0120161 A1* | 5/2009 | Ishiguro et al. | 73/23.21 |

FOREIGN PATENT DOCUMENTS

| | | |
|---|---|---|
| JP | 9-288085 A | 11/1997 |
| JP | 2004-212284 A | 7/2004 |
| JP | 2007-171024 A | 7/2007 |

* cited by examiner

*Primary Examiner* — Daniel Larkin
(74) *Attorney, Agent, or Firm* — Sughrue Mion, PLLC (57) ABSTRACT

A sensor control circuit unit (1) includes a circuit board (70) which has opposite sides (70a) and (70b) facing in parallel with each other, and carries a signal detection circuit (28) for receiving a detection signal whose level is equal to or less than one μA and which changes in accordance with $NO_X$ concentration, a power supply circuit (35), and a heater circuit (40) for controlling a heater. The power supply circuit (35) and the heater circuit (40) are mounted on one side of the circuit board (70) toward one side (70a) of the opposite sides, and the signal detection circuit (28) is mounted in a mounting area on the other side of the circuit board (70) toward the other side (70b) of the opposite sides, the mounting area being different from a mounting area of the circuits (35) and (40). A ground conductor (24x) connected to the ground is continuously formed on a surface of the circuit board (70) on which the signal detection circuit (28) is mounted such that the ground conductor (24x) extends along at least the other of the opposite sides.

9 Claims, 4 Drawing Sheets

SENSOR CONTROL UNIT AND GAS DETECTION APPARATUS

TECHNICAL FIELD

The present invention relates to a circuit unit for controlling a sensor (hereinafter referred to as a "sensor control circuit unit") connected to a gas sensor and including a circuit board on which a signal detection circuit, a power supply circuit, and a heater circuit are mounted, and to a gas detection apparatus which includes a sensor control circuit unit and a gas sensor connected thereto.

BACKGROUND ART

With tightening of regulation on exhaust gas of automobiles, reduction of the amount of nitrogen oxides ($NO_X$) within exhaust gas has been demanded, and $NO_X$ sensors capable of directly measuring the concentration of $NO_X$ contained in exhaust gas have been developed.

Such an $NO_X$ sensor includes a gas sensor element including a plurality of cells each composed of an oxygen-ion-conductive solid electrolyte layer formed of, for example, zirconia, and a pair of electrodes formed thereon, and detects the concentration of $NO_X$ on the basis of an output from the gas sensor element. Further, the gas sensor element includes a heater for activating the solid electrolyte layer.

The $NO_X$ sensor has a structure in which a first pumping cell, an oxygen concentration detection cell, a second pumping cell, and a heater are stacked. Each of the cells is composed of a solid electrolyte layer and a pair of electrodes formed thereon. The concentration of oxygen within a first measurement chamber is measured by the oxygen concentration detection cell, and the supply of electricity to the first pumping cell is controlled such that a to-be-measured gas (exhaust gas) introduced into the first measurement chamber has a predetermined oxygen concentration. That is, the current flowing through the first pumping cell is controlled such that the output of the oxygen concentration detection cell assumes a preset value, whereby the oxygen concentration of the to-be-measured gas is adjusted (controlled). Further, the to-be-measured gas having a controlled oxygen concentration flows from the first measurement chamber to a second measurement chamber. Through application of a constant voltage to the second pumping cell, $NO_X$ contained in the to-be-measured gas is decomposed to $N_2$ and $O_2$. At that time, a second pump current which flows between the pair of electrodes of the second pumping cell is measured, and the concentration of $NO_X$ contained in the to-be-measured gas is detected from the measured second pump current.

Such an $NO_X$ sensor requires various control circuits, such as a control circuit for adjusting the current flowing through the first pumping cell, a control circuit for maintaining the inter-electrode voltage of the second pumping cell constant, a circuit for detecting the second pump current, and a control circuit for controlling the supply of electricity to the heater so as to adjust generation of heat. In general, a sensor control circuit unit in which these circuits are mounted on a single circuit board is used. However, such a sensor control circuit unit in which various control circuits are mounted on a single circuit board has a problem in that noise (an influence of an electromagnetic field) from a heater circuit for controlling the supply of electricity to a heater enters a signal detection circuit for detecting the second pump current. The heater circuit is apt to generate noise because of ON/OFF control of the current supplied to the heater.

In a technique proposed in order to solve such a problem, a reference potential section is provided between a heater circuit and an Ip2 cell (second pumping cell) detection circuit so as to electrically isolate these circuits, to thereby prevent entry of noise into the Ip2 cell detection circuit (see Patent Document 1).

In another proposed technique, a ground pattern of a sensing circuit (corresponding to the above-mentioned Ip2 cell detection circuit) and a ground pattern of a heater drive circuit are separately provided on the opposite sides of a ground terminal (see Patent Document 2). According to this technique, variation in the reference potential (ground) of the sensing circuit is prevented, whereby the reference potential becomes stable, and, thus, the influence of noise from the heater drive circuit can be mitigated.

[Patent Document 1] Japanese Patent Application Laid-Open (kokai) No. 2007-171024

[Patent Document 2] Japanese Patent Application Laid-Open (kokai) No. 2004-212284

DISCLOSURE OF THE INVENTION

Problems to be Solved by the Invention

However, in the case of an $NO_X$ sensor including a plurality of cells each composed of a solid electrolyte layer and a pair of electrodes formed thereon, due to its complicated structure, a detection signal flowing through a cell (second pumping cell) in accordance with the concentration of $NO_X$ is weak, and its magnitude is equal to or less than one μA. Therefore, in the case of a detection circuit for detecting a weak detection signal which is equal to or less than one μA, such as an Ip2 cell (second pumping cell) detection circuit of a sensor control circuit unit connected to such an $NO_X$ sensor, noise must be further reduced to thereby improve the accuracy in detecting $NO_X$. Further, when measures are taken against noise entering a signal detection circuit which detects a detection signal corresponding to gas concentration, not only electromagnetic noise from circuits (heater circuits, etc.) other than the signal detection circuit, but also noise (external noise) from the outside of a circuit board must be taken into consideration.

That is, an object of the present invention is to provide a sensor control circuit unit which can reduce influence of noise on a signal detection circuit on a circuit board connected to a gas sensor to thereby improve the accuracy in detecting the concentration of a specific gas component, and to provide a gas detection apparatus which includes such an improved sensor control circuit unit.

Means for Solving the Problems

In order to solve the above-described problem, the present invention provides a sensor control circuit unit connected to a gas sensor which outputs a detection signal changing in accordance with concentration of a specific component, the sensor control circuit unit comprising a circuit board which has opposite sides facing in parallel with each other and which carries a signal detection circuit for receiving the detection signal, a power supply circuit for supplying a drive voltage to circuit elements mounted on the circuit board, and a heater circuit for controlling a heater which heats the sensor, wherein the power supply circuit and the heater circuit are mounted on one side of the circuit board toward one of the opposite sides, and the signal detection circuit is mounted in a mounting area on the other side of the circuit board toward the other of the opposite sides, the mounting area being different from a mounting area of the power supply circuit and the heater circuit; and a ground conductor connected to a ground is continuously formed on a surface of the circuit board on which the signal detection circuit is mounted such that the ground conductor extends along at least the other of the opposite sides.

According to this configuration, on the surface of the circuit board on which the signal detection circuit is mounted, the ground conductor surrounds the signal detection circuit so as to electrically shield the signal detection circuit to thereby reduce the influence of external noise on the detection signal through the signal detection circuit. Further, according to the sensor control circuit unit of the present invention, the signal detection circuit is disposed in a mounting area on the other side of the circuit board toward the other of the opposite sides, the mounting area being different from a mounting area of the power supply circuit and the heater circuit. Since the power supply circuit and the heater circuit, which handle currents whose magnitudes are larger than that of current flowing through the signal detection circuit, are disposed apart from the signal detection circuit, electromagnetic noise produced by the currents flowing through the power supply circuit and the heater circuit hardly affects the signal detection circuit. This circuit arrangement, coupled with the effect attained through provision of the ground conductor, can reduce the influence of noise on the signal detection circuit. Accordingly, in the present invention, the influence of noise on the signal detection circuit can be reduced, and the accuracy in detecting the concentration of the specific gas component can be improved.

Notably, the signal detection circuit is not limited to those which are formed on one surface of the circuit board, and may be those which are dividedly mounted on opposite surfaces (that is, front and back surfaces) of the circuit board. However, in the case where the signal detection circuit is dividedly formed on opposite surfaces of the circuit board, the above-mentioned ground conductor is formed on both the surfaces.

In the sensor control circuit unit of the present invention, the circuit board may have at least one ground layer located at a position different from the position of the ground conductor as viewed in a thickness direction of the circuit board; and the ground conductor may be electrically connected to the ground layer via a plurality of via conductors penetrating the circuit board.

According to this configuration, since the ground conductor is electrically connected to the at least one ground layer via the plurality of via conductors, the shield effect of the ground conductor against external noise can be enhanced. Notably, in order to obtain an excellent shield effect against external noise, preferably, the total volume of the ground layer(s) is greater than that of the ground conductor(s). Notably, in the present invention, the term "via conductor" refers to a conductor which extends through the circuit board in the thickness direction thereof.

In any of the above-described sensor control circuit units, the ground conductor may be continuously formed along the other of the opposite sides and at least one of sides adjacent to the other of the opposite sides.

According to this configuration, the ground conductor can surround the signal detection circuit more reliably. Therefore, the effect of electric shielding is enhanced, and the influence of external noise can be reduced further.

In any of the above-described sensor control circuit units, preferably, the ground conductor is formed such that the whole of outer edges of the ground conductor facing the corresponding sides of the circuit board are separated from the corresponding sides of the circuit board.

According to this configuration, even in the case where an external impact acts on a side of the circuit board when the circuit board is conveyed in a process for manufacturing the unit or is placed in a housing, damage to the ground conductor can be prevented without fail. In particular, if the ground conductor receives damage at the outer edge thereof with resultant formation of large irregularities, external noise is apt to concentrate at the irregularities, and the function of electric shielding is impaired. Therefore, the importance of the structure in which the outer edge of the ground conductor is separated from the corresponding side of the circuit board is large.

In any of the above-described sensor control circuit units, preferably, the ground conductor has a width of 1 mm or greater.

According to this configuration, the electrical shielding effect of the ground conductor against external noise can be attained effectively, whereby the influence of external noise on the signal detection circuit can be reduced further.

In any of the above-described sensor control circuit units, the ground conductor may have a ground extension portion which extends inward from a portion of the ground conductor along the surface of the circuit board such that at least a portion of the ground extension portion is present in an area of the surface in which the spacing between the mounting area of the power supply circuit and the heater circuit and the mounting area of the signal detection circuit becomes the smallest.

According to this configuration, the ground extension portion can suppress propagation of the influence of noise from the mounting area of the power supply circuit and the heater circuit to the mounting area of the signal detection circuit via a region where the spacing between the two mounting areas becomes the smallest.

In any one of the above-described sensor control circuit units, the gas sensor may be an $NO_X$ sensor which include a plurality of cells each composed of a solid electrolyte layer and a pair of electrodes formed thereon, and a heater for heating the cells, wherein one of the cells outputs a detection signal which changes in accordance with concentration of $NO_X$, which is the specific gas component, and the signal detection circuit detects the detection signal.

In an $NO_X$ sensor composed of a plurality of cells, due to its complicated structure, a detection signal flowing through a cell in accordance with the concentration of $NO_X$ is weak, and its magnitude is equal to or less than one $\mu A$. Therefore, the detection signal input to the signal detection circuit is also weak. When the unit of the present is used as a sensor control circuit unit applied to such an $NO_X$ sensor, the influence of external noise on the signal detection circuit is reduced, whereby the detection signal whose level is equal to or less than one $\mu A$ is effectively prevented from being affected by the external noise. The accuracy in detecting the concentration of $NO_X$ from the detection signal flowing through the signal detection circuit can be improved.

A gas detection apparatus according to the present invention includes the above-described sensor control circuit unit, and a sensor which outputs a detection signal changing in accordance with the concentration of the specific gas.

Effects of the Invention

According to the present invention, it is possible to provide a sensor control circuit unit and a gas detection apparatus which can reduce the influence of noise on the signal detection circuit on the circuit board connected to a sensor, to thereby improve the accuracy in detecting gas concentration.

MODE FOR CARRYING OUT THE INVENTION

An embodiment of the present invention will now be described.

First, a gas sensor ($NO_X$ sensor) which is connected to a sensor control circuit unit according to the embodiment of the present invention (hereinafter also referred to as the "controller") and which is controlled by the controller will be described. Notably, since the structure of the $NO_X$ sensor which is connected to the controller and which includes an $NO_X$ sensor element 10, a housing for accommodating the element 10, and lead wires connected to the element 10 is well known, in the following, the structure of the $NO_X$ sensor element 10 will be described with reference to FIG. 1, which shows a longitudinal cross section of the $NO_X$ sensor element 10.

Figure 1:
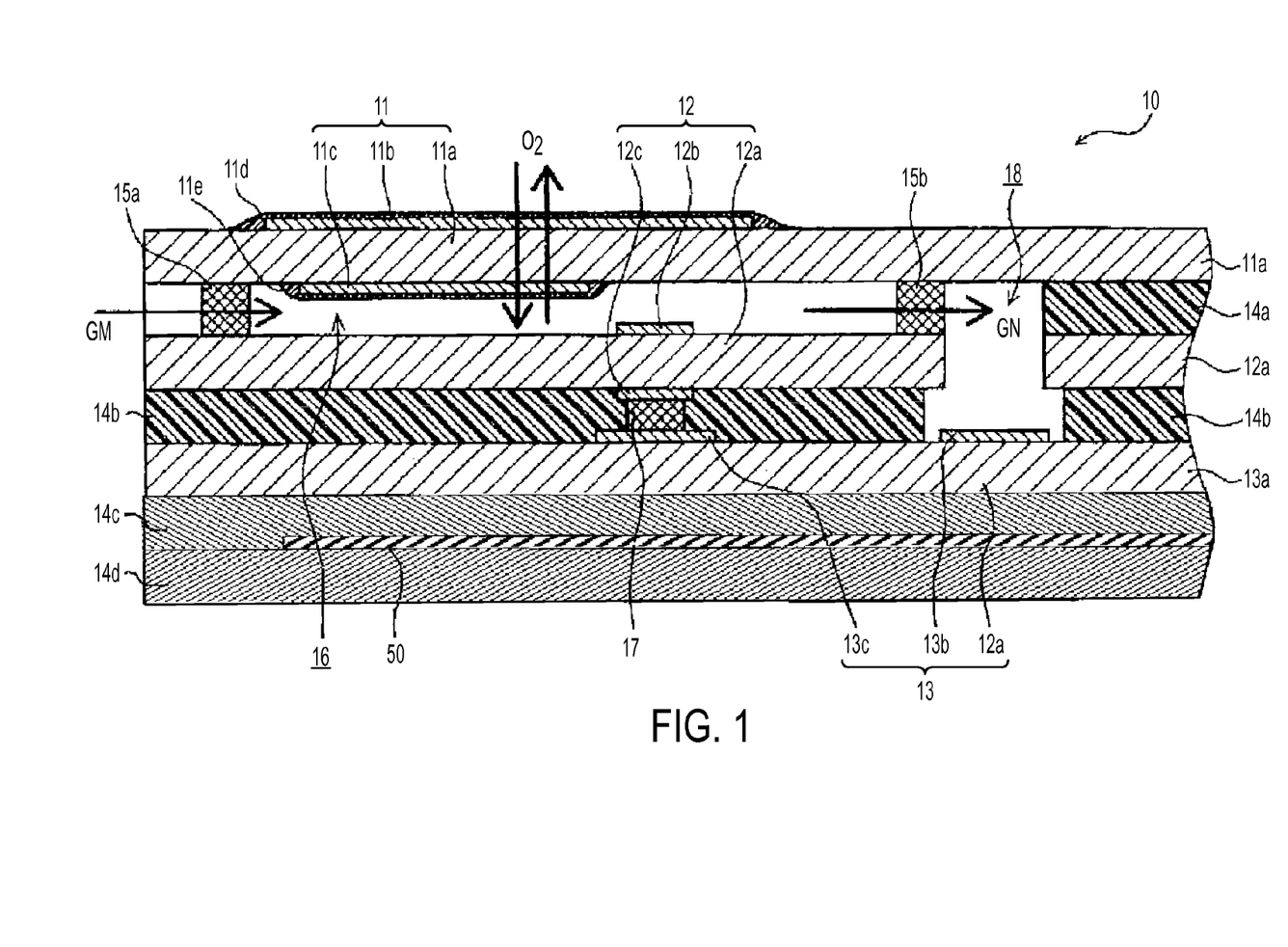
FIG. 1 Cross sectional view of an $NO_X$ sensor element taken along a longitudinal direction.

As shown in FIG. 1, the $NO_X$ sensor element 10 includes a first solid electrolyte layer 11a, an insulating layer 14a, a second solid electrolyte layer 12a, an insulating layer 14b, a third solid electrolyte layer 13a, and insulating layers 14c, 14d, which are stacked in this sequence. A first measurement chamber 16 is defined between the first solid electrolyte layer 11a and the second solid electrolyte layer 12a, and a to-be-measured gas GM is externally introduced into the first measurement chamber 16 via a first porous diffusion resistor 15a disposed at the left end (inlet) of the first measurement chamber 16.

A second porous diffusion resistor 15b is disposed at the end of the first measurement chamber 16 opposite the inlet. A second measurement chamber 18 defined on the right side of the first measurement chamber 16 communicates with the first measurement chamber 16 via the second diffusion resistor 15b. The second measurement chamber 18 is formed between the first solid electrolyte layer 11a and the third solid electrolyte layer 13a and extends through the second solid electrolyte layer 12a.

A heater 50 assuming the form of an elongated plate is disposed between the insulating layers 14c and 14d, and extends along the longitudinal direction of the $NO_X$ sensor element 10. The heater 50 heats the sensor to an activation temperature in order to enhance the oxygen-ion conductivity of the solid electrolyte layers, to thereby stabilize operation.

The insulating layers 14a to 14d are mainly formed of alumina, and the first diffusion resistor 15a and the second diffusion resistor 15b are formed of alumina. Further, the heater 50 is formed of platinum or any other suitable material.

A first pumping cell 11 includes the first solid electrolyte layer 11a, which is formed of zirconia having oxygen-ion conductivity, and an inner first pump electrode 11c and an outer first pump electrode (counterpart electrode) 11b disposed to sandwich the first solid electrolyte layer 11a. The inner first pump electrode 11c faces the first measurement chamber 16. Both the inner first pump electrode 11c and the outer first pump electrode 11b are mainly formed of platinum, and the surfaces of the electrodes 11b and 11c are covered with respective protective layers 11e and 11d each formed of a porous material.

Notably, the inner first pump electrode 11c is connected to a sensor terminal section 29a of a circuit board 70 to be described later, which constitutes the controller, and the outer first pump electrode 11b is connected to a sensor terminal section 29c of the circuit board 70 (see FIGS. 2 and 3).

An oxygen concentration detection cell 12 includes the second solid electrolyte layer 12a, which is mainly formed of zirconia, and a detection electrode 12b and a reference electrode 12c disposed to sandwich the second solid electrolyte layer 12a. The detection electrode 12b faces the first measurement chamber 16 at a location downstream of the inner first pump electrode 11c. Both the detection electrode 12b and the reference electrode 12c are mainly formed of platinum. The detection electrode 12b and the reference electrode 12c are connected to the sensor terminal section 29a and a sensor terminal section 29b, respectively, of the circuit board 70, which constitutes the controller (see FIGS. 2 and 3).

Notably, the insulating layer 14b is cut out to form a reference oxygen chamber 17, in which the reference electrode 12c in contact with the second solid electrolyte layer 12a is located, and which is filled with a porous material formed of alumina. An Ip1 cell/Vs cell control circuit 20, which will be described later, supplies a constant weak current to the oxygen concentration detection cell 12 in advance, so as to pump oxygen from the first measurement chamber 16 into the reference oxygen chamber 17, so that an oxygen reference atmosphere is created in the reference oxygen chamber 17.

A second pumping cell 13 includes the third solid electrolyte layer 13a mainly formed of zirconia, and an inner second pump electrode 13b and a second pump counterpart electrode 13c disposed on a surface of the third solid electrolyte layer 13a, which surface faces the second measurement chamber 18. Both the inner second pump electrode 13b and a second pump counterpart electrode 13c are mainly formed of platinum. The inner second pump electrode 13b is connected to the sensor terminal sections 29a of the circuit board 70, which constitutes the controller, and the second pump counterpart electrode 13c is connected to a sensor terminal sections 29d of the circuit board 70 (see FIGS. 2 and 3).

Notably, the second pump counterpart electrode 13c is disposed on the third solid electrolyte layer 13a to be located in the cut out portion of the insulating layer 14b, and faces the reference electrode 12c via the reference oxygen chamber 17.

Figure 2:
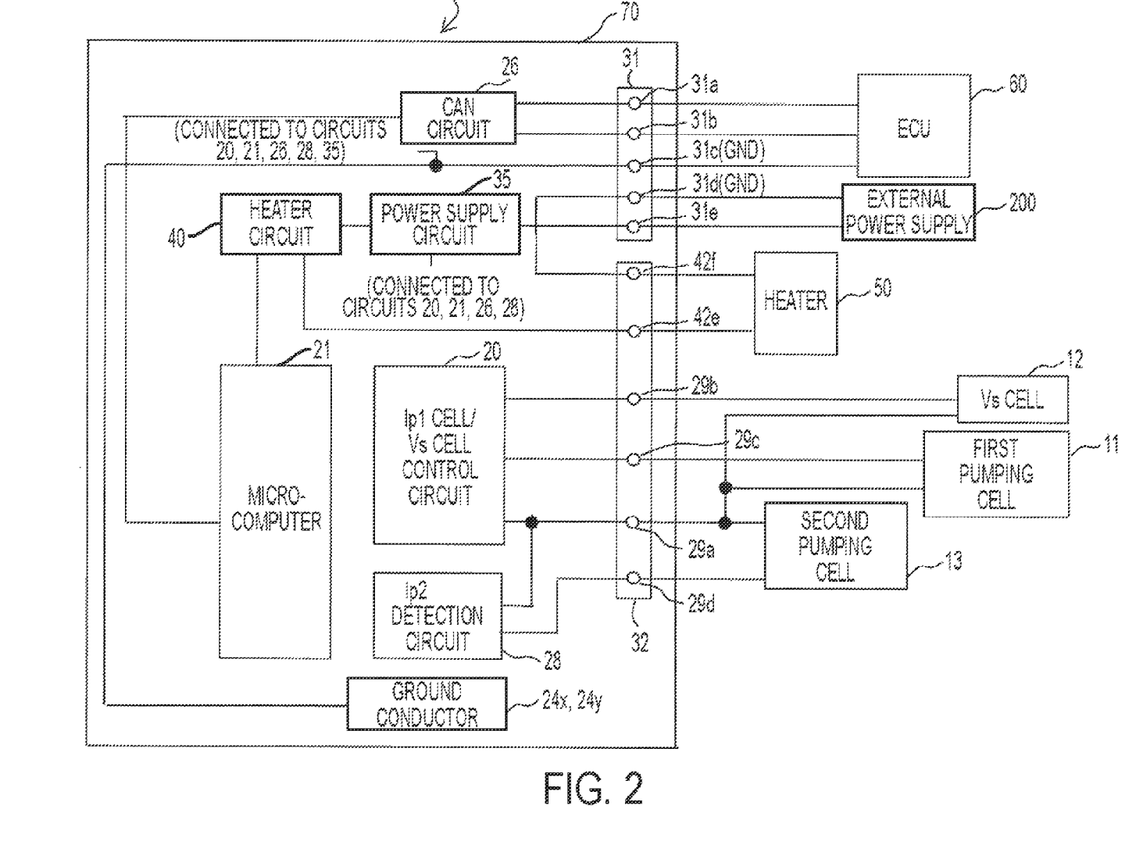
FIG. 2 Block diagram showing the configuration of a controller according to an embodiment of the invention.
Figure 3:
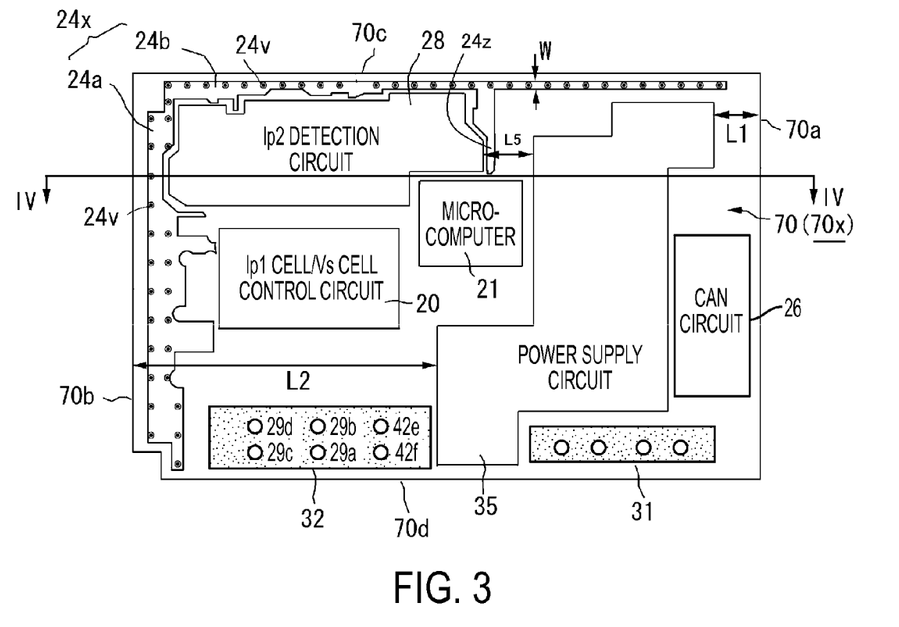
FIG. 3 View showing a specific circuit configuration of the controller.

Meanwhile, opposite ends of the heater 50 are connected to sensor terminal sections 42e and 42f, respectively, of the circuit board 70, which constitutes the controller, (see FIGS. 2 and 3).

Figure 6:
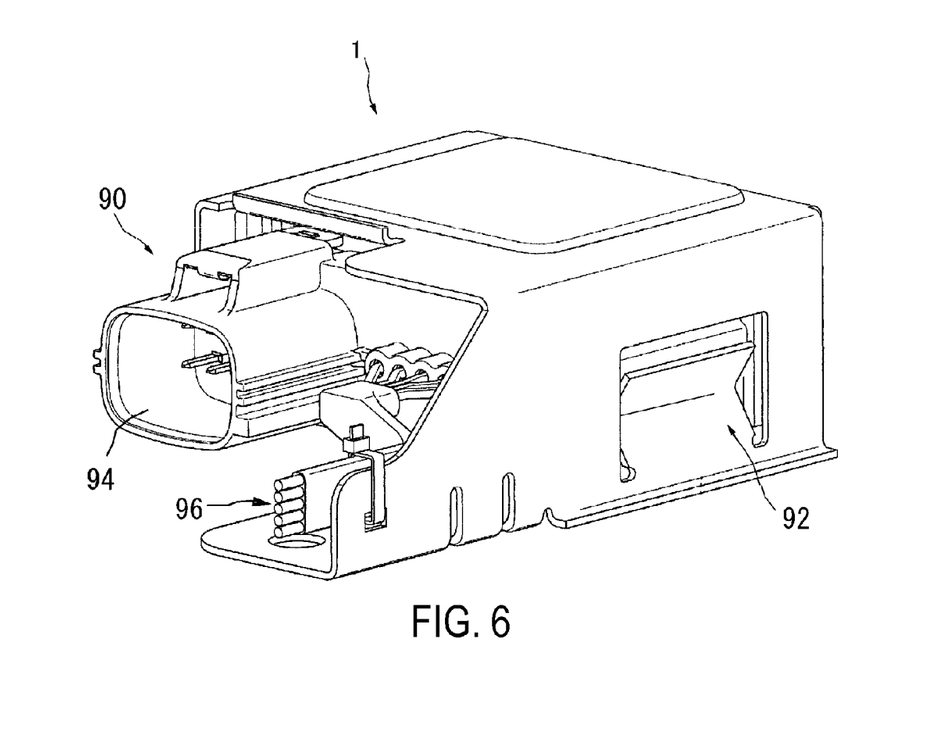
FIG. 6 Perspective view showing the structure of the controller, including a housing.

Next, the structure of the sensor control circuit unit (controller) 1 according to the embodiment of the present invention will be described. The controller 1 is connected to the $NO_X$ sensor ($NO_X$ sensor element 10) so as to constitute a gas detection apparatus, which is mounted on an unillustrated vehicle having an internal combustion engine (hereinafter also referred as the "engine"). Notably, as shown in FIG. 6, this controller 1 is composed of a housing 90 which is formed of resin and which accommodates the circuit board 70 to be described later, and a metallic cover 92 for vehicle mounting which holds the housing 90 therein. The resin housing 90 has a sensor connector 94 formed thereon, which is connected to a connector provided on a lead wire of the $NO_X$ sensor. Through this sensor connector 94, the sensor terminal sections 29a to 29d, 42e, and 42f of the circuit board accommodated within the housing 92 are electrically connected to the $NO_X$ sensor element 10 in the above-described manner. Further, signal wires 96 and an unillustrated connector for external equipment are provided on the housing 90 so as to establish electrical connection between the circuit board 70 and a vehicle-side engine control unit (hereinafter referred as the "ECU") 60 and an external power supply 200 (see FIG. 2).

As shown in the block diagram of FIG. 2, the controller 1 includes an ECU terminal section 31 and a sensor terminal section 32. The above-described sensor terminal sections 29a to 29d, 42e, and 42f are disposed in the sensor terminal section 32. The ECU terminal section 31 is electrically connected to the ECU 60 and the external power supply (e.g., a battery) 200. Specifically, the ECU terminal section 31 includes external connection terminals 31a and 31b which are connected to a CAN circuit 26 and through which a concentration signal representing the concentration of $NO_X$ calculated in a microcomputer 21 (corresponding to the $NO_X$ concentration converted from the detection signal), etc. are output to the ECU 60; an external connection terminal 31e which is electrically connected to the external power supply 200 and to which a power supply circuit 35 is connected; an external connection terminal 31d which is electrically connected to the ground of the external power supply and to which the sensor terminal section 42f is connected; and an external connection terminal 31c which is electrically connected to the ground of the ECU 60 and to which the various circuits 20, 26, 28, and 35, including the microcomputer 21, and ground conductors 24x, 24y to be described later are connected. Notably, the configuration of each circuit will be described later. The ECU 60 calculates the concentration of $NO_X$ contained in exhaust gas on the basis of a concentration signal, and performs various types of processing for control of the operation state of the engine, removal of $NO_X$ accumulated in catalyst, and detection of an anomalous state of the catalyst. That is, the controller 1 controls the supply of electricity to the $NO_X$ sensor element 10, and exchanges various signals, including the $NO_X$ concentration signal, with the ECU 60.

Notably, the external connection terminal 31c is electrically connected to a first ground layer 25a, which will be described later. Meanwhile, the external connection terminal 31d is electrically connected to a second ground layer 25b which forms a layer different from the first ground layer 25a and which will be described later, and is also electrically connected to the sensor terminal section 42f. That is, the circuits 20, 21, 26, 28, and 35 connected to the external connection terminal 31c are electrically connected to the first ground layer 25a, which is the ground of the signal system, and the sensor terminal section 42f connected to the external connection terminal 31d is electrically connected to the second ground layer 25b, which is the ground of the external power supply system.

On the circuit board 70, which constitutes the controller 1, there are mounted the Ip1 cell/Vs cell control circuit 20, the microcomputer (hereinafter referred to as the "MC") 21, the CAN circuit (an interface with a network of the vehicle) 26, the Ip2 detection circuit 28, the power supply circuit 35, and a heater circuit 40.

The MC 21, which controls the entire controller 1, includes an unillustrated CPU (central processing unit), ROM, and RAM. The CPU executes programs previously stored in the ROM, etc.

The power supply circuit 35 converts electric power supplied from the external power supply 200 to proper voltages used in the circuits (circuit elements) which constitute the controller 1, and supplies the voltages to the circuit elements as drive voltage.

The heater circuit 40 performs ON/OFF control of the supply of electricity to the heater 50 in accordance with a PWM signal received from the MC 21, and supplies the PWM-modulated electric power to the heater 50. That is, the heater circuit 40 supplies to the heater 50 electric power obtained through PWM modulation of the power supply voltage from the external power supply 200. As a result, the heater 50 heats the controller 1 to an activation temperature (e.g., 750° C.), and maintains it at a proper temperature at which the cells 11 to 13 function as solid electrolytes.

The Ip1 cell/Vs cell control circuit 20 controls the first pump current Ip1 flowing through the first pumping cell 11 such that a voltage Vs produced between the two electrodes of the oxygen concentration detection cell 12 becomes equal to a previously set constant voltage (e.g., 425 mV). That is, upon receipt of an instruction from the controller 1, the Ip1 cell/Vs cell control circuit 20 controls the direction and magnitude of the current flowing through the first pumping cell 11 such that the oxygen concentration within the first measurement chamber 16 of the $NO_X$ sensor element 10 is maintained at a constant level.

Upon receipt of an instruction from the controller 1, the Ip2 detection circuit 28 applies a predetermined second pump voltage Vp2 (e.g., 450 mV) to the second pumping cell 13. Further, at that time, the Ip2 detection circuit 28 detects, as a detection signal, the current which flows through the second pumping cell 13 and which represents the concentration of $NO_X$, and outputs the detection signal (specifically, a voltage signal converted from the current) to the controller 1. The Ip2 cell detection circuit 28 corresponds to the "signal detection circuit" in the claims.

Next, an example of operation of the $NO_X$ sensor element 10 and the controller 1 will be described. When the engine is started and the power supply circuit 35 receives electric power from the external power supply, the microcomputer 21 starts. As a result, the heater circuit 40 energizes the heater 50 to thereby heat the first pumping cell 11, the oxygen concentration detection cell 12, and the second pumping cell 13 to the activation temperature. Further, the microcomputer 21 drives the Ip1 cell/Vs cell control circuit 20 to thereby supply current of a constant magnitude to the oxygen concentration detection cell 12. Thus, the oxygen concentration detection cell 12 pumps oxygen from the first measurement chamber 16 into the reference oxygen chamber 17, whereby an oxygen reference atmosphere is created in the reference oxygen chamber 17.

After completion of heating of the cells 11 to 13 to the activation temperature, in response to an instruction from the microcomputer 21, the drive and control of the $NO_X$ sensor element 10, including all the cells 11, 12, and 13, are performed through use of the relevant circuits. The first pumping cell 11 adjusts the oxygen concentration of the to-be-measured gas (exhaust gas) GM introduced into the first measurement chamber 16 by pumping oxygen contained in the exhaust gas GM from the first measurement chamber 16 to the outside or pumping oxygen from the outside into the first measurement chamber 16.

At that time, the oxygen concentration within the first measurement chamber 16 corresponds to the inter-electrode voltage (voltage between the two electrodes) Vs of the oxygen concentration detection cell 12. Therefore, the Ip1 cell/Vs cell control circuit 20 controls the first pump current Ip1 flowing through the first pumping cell 11 such that the inter-electrode voltage Vs becomes equal to a constant voltage V1 (e.g., 425 mV).

The gas GN having been adjusted in terms of oxygen concentration further flows toward the second measurement chamber 18. The Ip2 cell detection circuit 28 applies a constant voltage V2 (e.g., 450 mV) to the second pumping cell 13 as the inter-electrode voltage (voltage between the electrodes) Vp. Since the constant voltage V2 is sufficiently high for decomposing the $NO_X$ gas within the gas GN to oxygen and $N_2$ gas, $NO_X$ is decomposed to nitrogen and oxygen. As a result, the second pump current Ip2 flows through the second pumping cell 13 so that the oxygen produced as a result of decomposition of $NO_X$ is pumped out of the second measurement chamber 18. Since an approximately linear relation is present between the second pump current Ip2 and the $NO_X$ concentration, the microcomputer 21 can detect the $NO_X$ concentration of the to-be-measured gas by detecting, as a detection signal, the second pump current Ip2 by use of the Ip2 detection circuit 28.

Next, the specific structure of the circuit board 70, which constitutes the controller 1, will be described with reference to FIGS. 3 and 4.

FIG. 3 is a plan view of the circuit board 70 schematically showing the circuit arrangement on the front side thereof. The Ip1 cell/Vs cell control circuit 20, the microcomputer 21, the CAN circuit 26, the Ip2 detection circuit 28, the power supply circuit 35, the sensor terminal section 32, and the ECU terminal section 31 are mounted on the front side 70x of the circuit board 70. Notably, in FIG. 3, solid lines which represents the circuits 20, 26, 28, 35, and the microcomputer 21 show respective mounting areas in which respective electronic parts of the circuits 20, 26, 28, 35, and the microcomputer 21 are mounted, and the electronic parts and wiring patterns are omitted from the drawings.

The circuit board 70 has a rectangular shape as viewed from above along the thickness direction thereof. This rectangular circuit board 70 has opposite sides 70a and 70b which face in parallel with each other and extend vertically. The power supply circuit 35 is mounted on the side toward the right side 70a. Meanwhile, the Ip2 detection circuit 28 is mounted on the side toward the left side 70b.

Herein, the expression "power supply circuit 35 is mounted on the side toward the right side 70a" means that the power supply circuit 35 is closer to the right side 70a than to the left side 70b. For example, the power supply circuit 35 is spaced from the right side 70a by a distance L1, and is spaced from the left side 70b by a distance L2. Since L1<L2, the power supply circuit 35 is determined to be mounted on the side toward the right side 70a.

Similarly, the Ip2 detection circuit 28 is determined to be mounted on the side toward the left side 70b.

Notably, the Ip2 detection circuit 28 is disposed on the side toward the left side 70b and along the upper side 70c, and the power supply circuit 35 occupies the greater part of the right half of the circuit board 70. Further, the microcomputer 21 is disposed below the Ip2 detection circuit 28 such that the microcomputer 21 is located at the approximate center of the circuit board 70, and the Ip1 cell/Vs cell control circuit 20 is disposed below the Ip2 detection circuit 28 to be located on the side toward the left side 70b of the circuit board 70.

The sensor terminal section 32 is disposed on the side toward the left side 70b and along the lower side 70d, and the ECU terminal section 31 is disposed on the side toward the right side 70a and along the lower side 70d. The CAN circuit 26 is disposed adjacent to the right side 70a.

Further, an L-shaped ground conductor 24x is continuously formed on the surface on the front side 70x of the circuit board 70 (the side on which the Ip2 detection circuit 28 is mounted) such that the ground conductor 24x extends along the left side 70b and the upper side 70c.

The ground conductor 24x is grounded (that is, is connected to the ground potential used for setting the reference potential in the Ip2 detection circuit). More specifically, the ground conductor 24x is composed of a first conductor 24a extending along the left side 70b, and a second conductor 24b extending along the upper side 70c adjacent to the left side 70b. The widths of the first conductor 24a and the second conductor 24b (as measured in the directions perpendicular to the left side 70b and the upper side 70c, respectively) are 1 mm or greater. Notably, the width W of the narrowest portion of the first conductor 24a and that of the second conductor 24b is 1 mm or greater.

The expression "the ground conductor is continuously formed" does not necessarily means the case where the ground conductor 24x is formed along the entirety of the left side 70b (or the upper side 70c), and encompasses the case where the ground conductor 24x is formed along the left side 70b (or the upper side 70c) at least over a distance greater than the corresponding length of an area where the Ip2 detection circuit 28 is formed.

The ground conductor 24x can be a trace of copper formed through etching.

Since the ground conductor 24x surrounds the Ip2 detection circuit 28 (signal detection circuit) on the circuit board 70 as described above, the ground conductor 24x can electrically shield the Ip2 detection circuit 28, which detects a weak current whose level is one μA or less, to thereby mitigate the influence of external noise on the detection signal flowing through the Ip2 detection circuit 28. Notably, in order to secure the effect of electrical shielding, preferably, the ground conductor 24x and a ground conductor 24y to be described later are formed such that the widths of the narrowest portions of these conductors 24x and 24y are 1 mm or greater.

Further, the Ip2 detection circuit 28 is disposed in a mounting area of the circuit board 70 which is located on the side toward the left side 70b (the other side) opposite the right side 70a (one side) and is different from the mounting area of the power supply circuit 35 and the heater circuit 40. Since the power supply circuit 35 and the heater circuit 40, which handle currents whose magnitudes are larger than that of current flowing through the Ip2 detection circuit 28, are disposed apart from the Ip2 detection circuit 28, electromagnetic noise produced by the currents flowing through the power supply circuit 35 and the heater circuit 40 hardly affects the Ip2 detection circuit 28. This circuit layout or arrangement, coupled with the effect attained through provision of the ground conductor 24x, can reduce the influence of noise on the Ip2 detection circuit 28.

Further, the ground conductor 24x is connected to a plurality of via conductors 24v extending through the circuit board 70.

Figure 4:
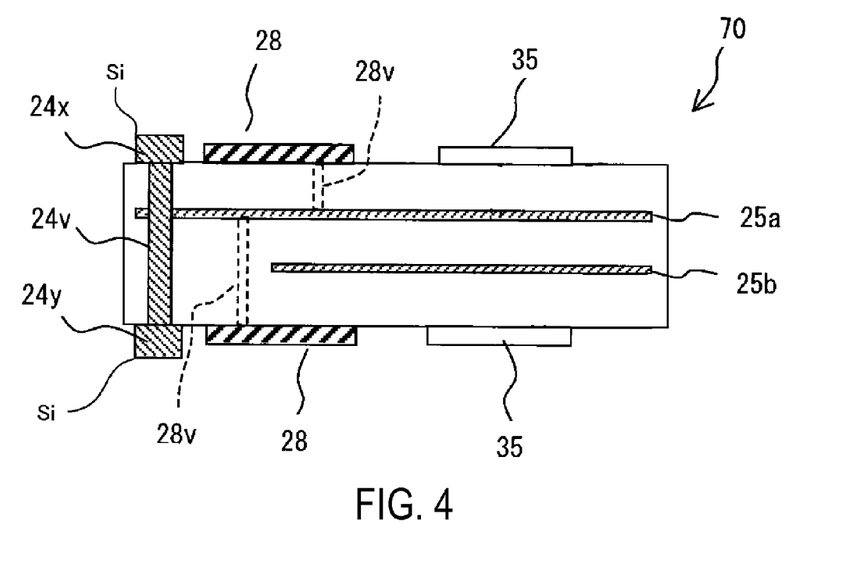
FIG. 4 Cross sectional view taken along line IV-IV of FIG. 3.

FIG. 4 is a cross sectional view taken along line IV-IV of FIG. 3. The circuit board 70 is a multilayer circuit board. The above-described first and second ground layers 25a and 25b are buried in the circuit board 70 with a predetermined insulating layer disposed therebetween such that the first and second ground layers 25a and 25b are located at different positions with respect to the thickness direction, and the first ground layer 25a is closer to the front side 70x of the circuit board 70 than is the second ground layer 25b. The plurality of via conductors 24v extend between the front side and back side of the circuit board 70 so as to establish electrical connection between the ground conductors 24x and 24y. The via conductors 24v are electrically connected to the first ground layer 25a.

Since the ground conductors 24x and 24y are electrically connected to the first ground layer 25a via the plurality of via conductors 24v as described above, the shield effect of the ground conductors against external noise is enhanced. Notably, in order to obtain an excellent shield effect against external noise, preferably, the total volume of the ground layers is greater than that of the ground conductors. Notably, the first ground layer 25a corresponds to the "ground layer" in the claims. Further, the via conductors 24v may have a diameter of about 0.4 mm.

As having already been described, the first ground layer 25a is connected to the external connection terminal 31c. Thus, the circuits (the MC 21, the Ip2 detection circuit 28, etc.) are connected to the first ground layer 25a, which serves as a ground for the signal system, via the wiring on the surface of the circuit board 70 and conductors (via conductors) penetrating the circuit board 70, and, thus, is electrically connected to the external connection terminal 31c. For example, the Ip2 detection circuit 28 is connected to the first ground layer 25a via the via conductors 28v. Notably, although not shown in FIG. 4, the power supply circuit 35 is also connected to the first ground layer 25a via a via conductor at a position different from the position of the cross section of FIG. 4.

Meanwhile, the second ground layer 25b is connected to neither the ground conductors 24x and 24y nor the via conductors 24v, and solely forms a ground for the external power supply system. As having already being described, the second ground layer 25b is connected to the external connection terminal 31d. Thus, although not shown in the drawing, the sensor terminal section 42f connected to one end of the heater 50 is connected to the second ground layer 25b, which serves as the ground for the external power supply system, via the wiring on the surface of the circuit board 70 and conductors (via conductors) penetrating the circuit board 70, and, thus, is electrically connected to the external connection terminal 31d.

Figure 5:
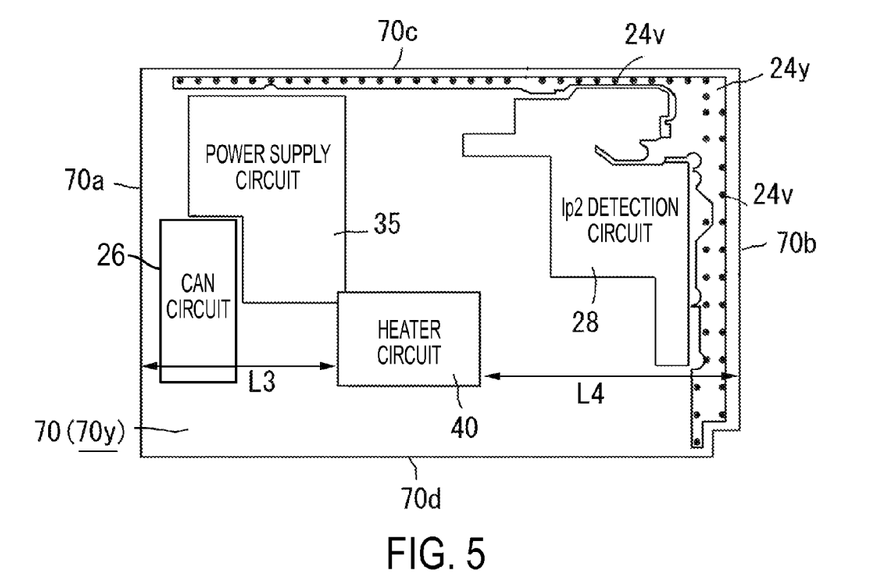
FIG. 5 Another view showing the specific circuit configuration of the controller.

FIG. 5 is a plan view of the circuit board 70 as viewed from the back side 70y, schematically showing the circuit arrangement. The CAN circuit 26, the Ip2 detection circuit 28, the power supply circuit 35, and the heater circuit 40 are mounted on the back side 70y of the circuit board 70. Notably, the plan view of this FIG. 5 shows the back side 70y of the circuit board 70, which appears when the circuit board 70 is turned over from the posture shown in FIG. 3 about the right side 70a, and, in FIG. 5, the right side 70a shown in FIG. 3 is located on the left side. Notably, in FIG. 5 as well, solid lines which represent the circuits 26, 28, 35, and 40 show respective mounting areas in which respective electronic parts of the circuits 26, 28, 35, and 40 are mounted, and the electronic parts and wiring patterns are omitted from the drawings.

As shown in FIG. 5, the power supply circuit 35 occupies about one third of the left side (the side toward the right side 70a) of the circuit board 70. Further, the heater circuit 40 is located at a position slightly offset from the center of the circuit board 70 toward the lower side 70d.

Meanwhile, the Ip2 detection circuit 28 is mounted on the side toward the left side 70b, and an inverted-L-shaped ground conductor 24y is continuously formed on the back side 70y of the circuit board 70 along the left side 70b and the upper side 70c. Notably, in the present embodiment, since the Ip2 detection circuit 28 is dividedly mounted on the front and back sides (opposite sides) of the circuit board 70, the ground conductors 24x and 24y are formed on the opposite sides of the circuit board 70. Notably, in the case where the Ip2 detection circuit 28 is mounted on only one side of the circuit board 70, the ground conductor is formed only on the side where the Ip2 detection circuit 28 is mounted.

The heater circuit 40 is also mounted on the side toward the right side 70a. That is, the heater circuit 40 is spaced from the right side 70a by a distance L3 and is spaced from the left side 70b by a distance L4, and a relation L3<L4 is satisfied.

In the present embodiment, the power supply circuit 35 and the heater circuit 40, which are apt to generate noise (electromagnetic noise) because of their currents greater in magnitude than the current flowing through the Ip2 detection circuit 28, are disposed on the side toward the right side 70a, and the Ip2 detection circuit 28 is disposed on the side toward the left side 70b. Thus, the Ip2 detection circuit 28 is disposed in a mounting area different from the mounting area of the power supply circuit 35 and the heater circuit 40. Therefore, the influence, on the Ip2 detection circuit 28, of noise from the power supply circuit 35 and the heater circuit 40 can be reduced.

Further, in the present embodiment, as shown in FIGS. 3 and 5, the ground conductors 24x and 24y are formed on the circuit board 70 such that outer edges (portions indicated by symbol "Si" in FIG. 4) facing the corresponding sides (the left side 70b and the upper side 70c) of the circuit board 70 are separated from the left side 70b and the upper side 70c, respectively. By virtue of this configuration, even in the case where an external impact acts on a side of the circuit board 70 when the circuit board 70 is conveyed in a process for manufacturing the unit or the circuit board 70 is placed in the housing 90, damage to the outer edges of the ground conductors 24x and 24y can be prevented without fail. In particular, if at least one of the ground conductors 24x and 24y receives damage at the outer edge thereof with resultant formation of large irregularities, external noise concentrates at the irregularities, and the function of electric shielding is impaired. Therefore, the importance of the structure in which the outer edges of the ground conductors 24x and 24y are separated from the corresponding sides (the left side 70b and the upper side 70c) of the circuit board 70 is large.

As can be found through comparison between the front and back sides 70x and 70y of the circuit board 70, in the present embodiment, the spacing between the mounting area of the power supply circuit 35 and the heater circuit 40 and the mounting area of the Ip2 detection circuit 28 becomes the smallest on the front side 70x of the circuit board 70 (at a location indicated by L5 in FIG. 3). In the present embodiment, since the above-mentioned two mounting areas are separated from each other, the influence, on the Ip2 detection circuit 28, of noise from the power supply circuit 35 and the heater circuit 40 is reduced. However, at the position at which the spacing between the two mounting areas becomes the smallest, the Ip2 detection circuit 28 may be affected by the noise.

In order to solve such a problem, in the present embodiment, the ground conductor 24x has a ground extension portion 24z as shown in FIG. 3. Specifically, the ground extension portion 24z extends from a portion of the ground conductor 24x inward along the surface of the circuit board 70 such that a portion of the ground extension portion 24z is present in an area where the spacing between the mounting area of the power supply circuit 35 and the heater circuit 40 (in the present embodiment, the mounting area of the power supply circuit 35) and the mounting area of the Ip2 detection circuit 28 becomes the smallest. This configuration can more reliably prevent propagation of the influence of noise from the mounting area of the power supply circuit 35 and the heater circuit 40 (in the present embodiment, the mounting area of the power supply circuit 35) to the mounting area of the Ip2 detection circuit 28.

Needless to say, the present invention is not limited to the above-described embodiment, and encompasses various modifications and equivalents which fall within the scope of the invention. For example, a squarish-C shaped ground conductor may be continuously formed along the left side 70b, the upper side 70c, and the lower side 70d of the circuit board 70. However, the ground conductor should not be provided along sides close to the power supply circuit 35 or the heater circuit 40, which generates noise, (in the above-described example, the right side 70a, and the lower side 70d on the back side 70y of the circuit board 70). This is because the ground conductor may catch noise (electromagnetic noise) from the power supply circuit 35 or the heater circuit 40.

In the above-described embodiment, the $NO_X$ sensor element includes three solid electrolyte layers. However, an $NO_X$ sensor element including two solid electrolyte layers may be employed. The structure of an $NO_X$ sensor element including two solid electrolyte layers is disclosed in, for example, Japanese Patent Application Laid-Open (kokai) No. H9-288085 (FIG. 2).

The present invention can be applied to a gas sensor for detecting the concentration of $NO_X$ gas contained in exhaust gas of automobiles and various types of internal combustion engines, or combustion gas of boilers or the like. However, the application of the present invention is not limited thereto. For example, the present invention can be applied to a gas sensor which includes a gas sensor element for detecting the concentration of gas other than $NO_X$ (e.g., $CO_X$, $H_2O$, HC).

DESCRIPTION OF REFERENCE NUMERALS

1: sensor control circuit unit (controller)
10: sensor ($NO_X$ sensor element)
11: first pumping cell
12: oxygen concentration detection cell
13: second pumping cell
24x, 24y: ground conductor
24v: via conductor
24z: ground extension portion
25a: first ground layer (ground layer)
28: signal detection circuit (Ip2 detection circuit)
35: power supply circuit
40: heater circuit
70: circuit board
70a: one of opposite sides (one side)
70b: the other of opposite sides (the other side)
70c, 70d: sides adjacent to the other side
70x: front side of the circuit board
70y: back side of the circuit board
90: housing
100: gas detection apparatus

The invention claimed is:

1. A sensor control circuit unit connected to a gas sensor which outputs a detection signal changing in accordance with concentration of a specific component, the sensor control circuit unit comprising a circuit board which has opposite sides facing in parallel with each other and which carries a signal detection circuit for receiving the detection signal, a power supply circuit for supplying a drive voltage to circuit elements mounted on the circuit board, and a heater circuit for controlling a heater which heats the sensor, wherein the power supply circuit and the heater circuit are mounted on one side of the circuit board toward one of the opposite sides, and the signal detection circuit is mounted in a mounting area on the other side of the circuit board toward the other of the opposite sides, the mounting area being different from a mounting area of the power supply circuit and the heater circuit; and a ground conductor connected to a ground is continuously formed on a surface of the circuit board on which the signal detection circuit is mounted such that the ground conductor extends along at least the other of the opposite sides.

2. A sensor control circuit unit according to claim 1, wherein the circuit board has at least one ground layer located at a position different from the position of the ground conductor as viewed in a thickness direction of the circuit board; and the ground conductor is electrically connected to the at least one ground layer via a plurality of via conductors penetrating the circuit board.

3. A sensor control circuit unit according to claim 1, wherein the ground conductor is continuously formed along the other of the opposite sides and at least one of sides adjacent to the other of the opposite sides.

4. A sensor control circuit unit according to claim 1, wherein the ground conductor is formed such that the whole of outer edges of the ground conductor facing the corresponding sides of the circuit board are separated from the corresponding sides of the circuit board.

5. A sensor control circuit unit according to claim 1, wherein the ground conductor has a width of 1 mm or greater.

6. A sensor control circuit unit according to claim 1, wherein the ground conductor has a ground extension portion which extends inward from a portion of the ground conductor along the surface of the circuit board such that at least a portion of the ground extension portion is present in an area of the surface in which the spacing between the mounting area of the power supply circuit and the heater circuit and the mounting area of the signal detection circuit becomes the smallest.

7. A sensor control circuit unit according to claim 1, wherein the gas sensor is an $NO_X$ sensor which includes a plurality of cells each composed of a solid electrolyte layer and a pair of electrodes formed thereon, and a heater for heating the cells, wherein one of the cells outputs a detection signal which changes in accordance with concentration of $NO_X$, which is the specific gas component, and the signal detection circuit detects the detection signal.

8. A gas detection apparatus comprising a sensor control circuit unit according to claim 1, and a sensor which outputs a detection signal changing in accordance with the concentration of the specific gas.

9. A sensor control circuit according to claim 1, wherein the gas sensor includes a gas sensor element for detecting the concentration of a gas selected from the group consisting of NOx, COx, $H_2O$ and HC.

\* \* \* \* \*